United States Patent
Jang et al.

(10) Patent No.: US 11,452,627 B2
(45) Date of Patent: Sep. 27, 2022

(54) STENT DELIVERY DEVICE

(71) Applicant: IUCF-HYU (INDUSTRY-UNIVERSITY COOPERATION FOUNDATION HANYANG UNIVERSITY), Seoul (KR)

(72) Inventors: Gunhee Jang, Seoul (KR); Wonseo Lee, Yongin-si (KR); Jae Kwang Nam, Goyang-si (KR); Eun Soo Jung, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 275 days.

(21) Appl. No.: 16/633,880

(22) PCT Filed: Jun. 18, 2018

(86) PCT No.: PCT/KR2018/006840
§ 371 (c)(1),
(2) Date: Jan. 24, 2020

(87) PCT Pub. No.: WO2019/022380
PCT Pub. Date: Jan. 31, 2019

(65) Prior Publication Data
US 2020/0197202 A1    Jun. 25, 2020

(30) Foreign Application Priority Data
Jul. 25, 2017 (KR) .......................... 10-2017-0094360

(51) Int. Cl.
*A61F 2/95* (2013.01)
*A61F 2/06* (2013.01)
*A61F 2/04* (2013.01)

(52) U.S. Cl.
CPC .................. *A61F 2/95* (2013.01); *A61F 2/06* (2013.01); *A61F 2002/041* (2013.01);
(Continued)

(58) Field of Classification Search
CPC ...... A61F 2/95; A61F 2/06; A61F 2002/9505; A61F 2210/009; A61B 17/00234;
(Continued)

(56) References Cited

U.S. PATENT DOCUMENTS 5,817,100 A   10/1998 Igaki
5,951,566 A   9/1999 Lev
(Continued)

FOREIGN PATENT DOCUMENTS

JP   2009-530060 A   8/2009
JP   2010-540170 A   12/2010
(Continued)

OTHER PUBLICATIONS

International Search Report of PCT/KR2018/006840 dated Sep. 20, 2018.

*Primary Examiner* — Jennifer Dieterle
*Assistant Examiner* — Tiffany P Shipmon
(74) *Attorney, Agent, or Firm* — Sughrue Mion, PLLC (57) ABSTRACT

The present invention relates to a stent delivery device having: a first support rod into which a first movable body is inserted; a fixed magnet; and a second support rod into which a second movable body is inserted, wherein a first driving magnet included in the first movable body and a second driving magnet included in the second movable body rotate relative to each other by means of the control of an (Continued)

external magnetic field at a predetermined angle around an axis in a first direction with respect to the fixed magnet, thereby separating a first coupling piece and a second coupling piece from a first coupling groove and a second coupling groove and enabling a stent to unfold.

9 Claims, 5 Drawing Sheets (52) U.S. Cl.
CPC ... *A61F 2002/043* (2013.01); *A61F 2002/044* (2013.01); *A61F 2002/047* (2013.01); *A61F 2002/9505* (2013.01); *A61F 2210/009* (2013.01)

(58) Field of Classification Search
CPC ... A61B 17/315; A61B 17/3423; A61B 17/11; A61B 17/3421; A61B 17/7016; A61B 2017/00039
See application file for complete search history.

(56) References Cited

U.S. PATENT DOCUMENTS

| | | |
|---|---|---|
| 8,419,681 B2 | 4/2013 | Sell |
| 2004/0087899 A1 | 5/2004 | Weber et al. |
| 2013/0297002 A1 | 11/2013 | Igaki |

FOREIGN PATENT DOCUMENTS

| | | |
|---|---|---|
| KR | 10-0342025 B1 | 3/2003 |
| KR | 10-2011-0095479 A | 8/2011 |
| KR | 10-2012-0089056 A | 8/2012 |
| KR | 10-2013-0096646 A | 8/2013 |
| KR | 10-2014-0030353 A | 3/2014 |

STENT DELIVERY DEVICE

CROSS REFERENCE TO RELATED APPLICATIONS

This application is a National Stage of International Application No. PCT/KR2018/006840 filed Jun. 18, 2018, claiming priority based on Korean Patent Application No. 10-2017-0094360 filed Jul. 25, 2017.

BACKGROUND OF THE INVENTION

1. Field of the Invention

The present invention relates to a stent delivery device, and more particularly, to a stent delivery device inserted into a human body to expand a stent.

2. Description of the Prior Art

A self-expandable stent is used to improve stenosis or occlusion occurring in a body tubular cavity such as blood vessel, bile duct, bronchus, esophagus, and urethra. The self-expandable stent is formed in a cylindrical shape as a whole using a metal wire or the like, and expandable in the body tubular cavity.

Typically, according to a basic approach for delivering the self-expandable stent, the stent moves forward through a sleeve or catheter by pushing the stent in a distal direction through the sleeve or catheter until the stent comes out of a distal end of the sleeve or catheter at a desired position within a patient's vasculature.

According to the above conventional approach for delivering the stent, the catheter is inserted into a human body and positioned at a stenosed lesion and then an operator expands the stent by manually operating the catheter. However, there is a disadvantage in that it is difficult for the operator to precisely maintain the position of an end of the catheter while applying a momentary large force to the catheter using both hands so as to expand the stent.

SUMMARY OF THE INVENTION

The present invention provides a stent delivery device capable of expanding a stent using an external magnetic field.

Technical Solution

The stent delivery device serves as a device for mounting a stent and includes: an inner body in which a first support rod, a fixed magnet, and a second support rod are sequentially coupled to each other in a first direction; a first movable body inserted into the first support rod, and having one end, which is adjacent to the fixed magnet, coupled to a first driving magnet and an opposite end formed with a first coupling groove to which a first coupling piece formed in the first support rod is inserted; and a second movable body inserted into the second support rod, and having one end, which is adjacent to the fixed magnet, coupled to a second driving magnet and an opposite end formed with a second coupling groove to which a second coupling piece formed in the second support rod is inserted, wherein the stent is fastened to surround the first movable body, the fixed magnet, and the second movable body, each of the first driving magnet and the second driving magnet is relatively rotated by control of an external magnetic field with respect to the fixed magnet about a first direction to allow polarity same as polarity of the fixed magnet to be arranged in series in the first direction, and the first movable body and the second movable body are rotated together with the first driving magnet and the second driving magnet, respectively, so that coupling between the first coupling piece and the first coupling groove and coupling between the second coupling piece and the second coupling groove may be released.

In addition, the inner body may further include nonmagnetic spacers provided between the fixed magnet and the first driving magnet and between the fixed magnet and the second driving magnet, respectively.

In addition, the stent delivery device may further include a first elastic body inserted into the first movable body, compressed when the first coupling piece is coupled to the first coupling groove, and delivering an elastic force to the first movable body when the first coupling piece is released from the first coupling groove; and a second elastic body inserted into the second movable body, compressed when the second coupling piece is coupled to the second coupling groove, and delivering an elastic force to the second movable body when the second coupling piece is released from the second coupling groove.

In addition, a front end of the first movable body may be formed with a first protrusion for supporting one end of the first elastic body, and a rear end of the second movable body may be formed with a second protrusion for supporting one end of the second elastic body, in which the first movable body may be relatively rotatable to the first protrusion, and the second movable body may be relatively rotatable to the second protrusion.

In addition, polarity of the first driving magnet is arranged to be offset from polarity of the fixed magnet by a predetermined angle about the first direction when the first coupling piece is coupled to the first coupling groove, and polarity of the second driving magnet may be arranged to be offset from the polarity of the fixed magnet by a predetermined angle about the first direction when the second coupling piece is coupled to the second coupling groove.

In addition, each of the fixed magnet, the first driving magnet, and the second driving magnet may be bisected into N pole and S pole about the first direction. In addition, the stent delivery device may further include a first stent cover fixedly coupled to the opposite end of the first movable body to accommodate one end of the stent; and a second stent cover fixedly coupled to the opposite end of the second movable body to accommodate an opposite end of the stent.

In addition, the first movable body may be formed with a first guide groove provided in the first direction and connected to the first coupling groove, and the second movable body may be formed with a second guide groove provided in the first direction and connected to the second coupling groove, in which the first coupling piece may be positioned in the first guide groove when the first coupling piece is released from the first coupling groove, and the second coupling piece may be positioned in the second guide groove when the second coupling piece is released from the second coupling groove.

Advantageous Effects

According to the present invention, a magnetic pulley device inserted into the human body may be controlled from the outside of the human body by using the external magnetic field, so that the stent can be expanded in a wireless manner.

In addition, according to the present invention, the magnetic pulley device may be operated by the control of the external magnetic field without a manual operation of the operator, so that the expansion of the stent can be precisely controlled.

BRIEF DESCRIPTION OF THE DRAWINGS

The above and other objects, features, and advantages of the present invention will be more apparent from the following detailed description taken in conjunction with the accompanying drawings, in which.

DETAILED DESCRIPTION OF THE EXEMPLARY EMBODIMENTS

The stent delivery device serves as a device for mounting a stent, and includes an inner body in which a first support rod, a fixed magnet, and a second support rod are sequentially coupled to each other in a first direction; a first movable body inserted into the first support rod, and having one end, which is adjacent to the fixed magnet, coupled to a first driving magnet and an opposite end formed with a first coupling groove to which a first coupling piece formed in the first support rod is inserted; and a second movable body inserted into the second support rod, and having one end, which is adjacent to the fixed magnet, coupled to a second driving magnet and an opposite end formed with a second coupling groove to which a second coupling piece formed in the second support rod is inserted, wherein the stent is fastened to surround the first movable body, the stator magnet, and the second movable body, each of the first driving magnet and the second driving magnet is relatively rotated by control of an external magnetic field with respect to the fixed magnet about a first direction to allow polarity same as polarity of the fixed magnet to be arranged in series in the first direction, and the first movable body and the second movable body are rotated together with the first driving magnet and the second driving magnet, so that coupling between the first coupling piece and the first coupling groove and coupling between the second coupling piece and the second coupling groove may be released.

Hereinafter, exemplary embodiments of the present invention will be described in detail with reference to the accompanying drawings. However, the technical idea of the present invention is not limited to the exemplary embodiments described herein and may be embodied in other forms. Further, the embodiments disclosed herein may be provided such that the disclosed features can be thorough and complete and the idea of the present invention can be fully understood by those skilled in the art.

In the specification herein, when one component is mentioned as being on another component, it signifies that the one component may be placed directly on another component or a third component may be interposed therebetween. In addition, in drawings, thicknesses of films and regions may be exaggerated to effectively describe the technology of the present invention.

In addition, although terms such as first, second and third are used to describe various components in various embodiments of the present specification, the components should not be limited by the terms. The above terms are used merely to distinguish one component from another. Accordingly, a first component referred to in one embodiment may be referred to as a second component in another embodiment. Each embodiment described and illustrated herein may also include a complementary embodiment. In addition, the term "and/or" is used herein to include at least one of the components listed before and after the term.

The singular expression herein includes a plural expression unless the context clearly specifies otherwise. In addition, it should be understood that the term such as "include" or "have" herein is intended to designate the presence of feature, number, step, component, or a combination thereof recited in the specification, and does not preclude the possibility of the presence or addition of one or more other features, numbers, steps, components, or combinations thereof. In addition, the term "connection" herein is used to include both indirect connection of a plurality of components and direct connection of the components.

In addition, in the following description of the embodiments of the present invention, the detailed description of known functions and configurations incorporated herein will be omitted when it possibly makes the subject matter of the present invention unclear unnecessarily.

Figure 1:
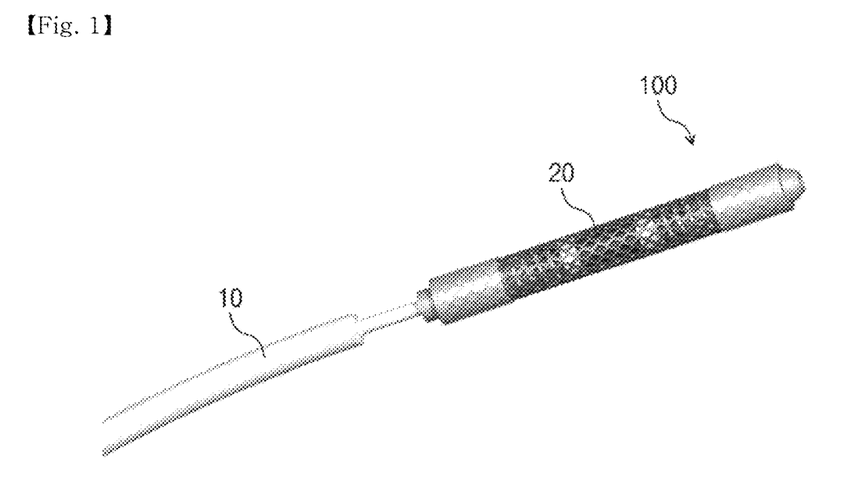
FIG. 1 is a perspective view showing a stent delivery device coupled to a catheter according to an embodiment of the present invention.
Figure 2:
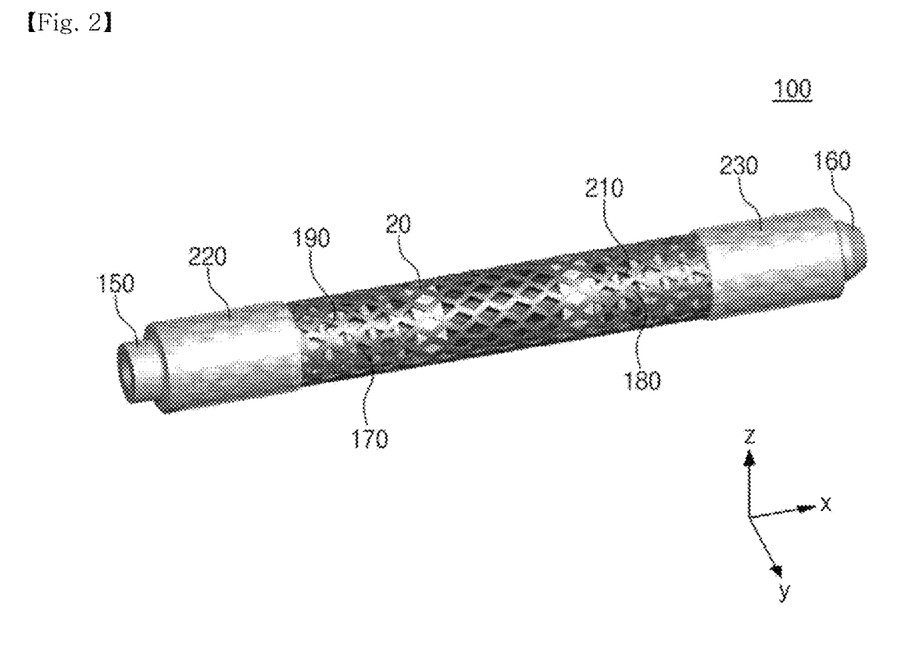
FIG. 2 is a perspective view showing the stent delivery device of FIG. 1.
Figure 3:
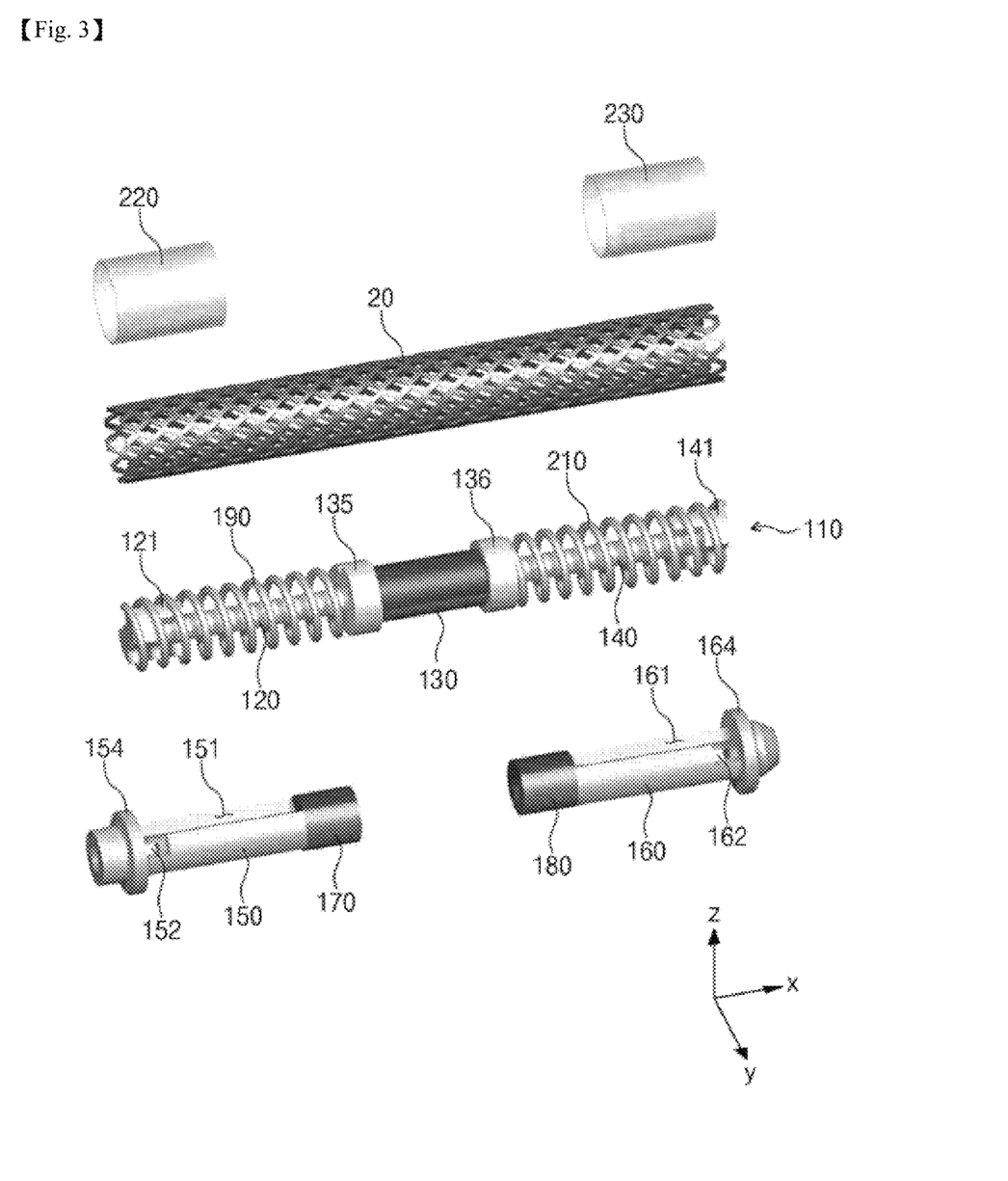
FIG. 3 is an exploded perspective view showing the stent delivery device of FIG. 2.

FIG. 1 is a perspective view showing a stent delivery device coupled to a catheter according to an embodiment of the present invention. FIG. 2 is a perspective view showing the stent delivery device of FIG. 1. FIG. 3 is an exploded perspective view showing the stent delivery device of FIG. 2.

Referring to FIGS. 1 to 3, a stent delivery device 100 is mounted to a catheter 10 and inserted into a human body, and expands a stent 20. The stent delivery device 100 may be positioned in a cavity (such as pleural cavity and peritoneal cavity), a tubular organ (such as bronchus, esophagus, stomach, intestine, bladder, ureter, and blood vessel) or the like in a human body to expand the stent 20.

The stent 20 is expanded by the stent delivery device 100 in the human organ having a narrowed or occluded passage to secure the passage. The stent 20 is a net tube device and may be provided as a self-expandable type.

The stent delivery device 100 includes an inner body 110, first and second movable bodies 150 and 160, first and second driving magnets 170 and 180, first and second elastic bodies 190 and 210, and first and second stent covers 220 and 230.

The inner body 110 is provided to have a structure in which a first support rod 120, a fixed magnet 130, and a second support rod 140 are sequentially coupled to each other in one direction. Hereinafter, the direction for coupling the first support rod 120, the fixed magnet 130, and the second support rod 140 is referred to as a first direction X.

The first support rod 120 and the second support rod 140 are rods having a predetermined length and are provided at both sides of the fixed magnet 130, respectively. A front end of the first support rod 120 is spaced apart from the fixed magnet 130 and coupled to the catheter 10. A first coupling piece 121 is formed at the front end of the first support rod 120.

Figure 4:
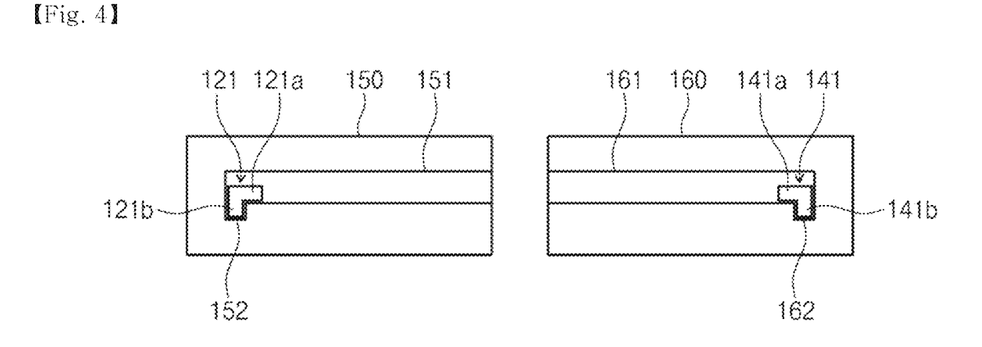
FIG. 4 is a view showing coupling relationships between the first and second movable bodies and the first and second coupling bodies, respectively.

FIG. 4 is a view showing coupling relationships between the first and second movable bodies and the first and second coupling bodies, respectively.

Referring to FIG. 4, the first coupling piece 121 includes a first region 121a arranged in parallel with the first direction X, and a second region 121b extending in a vertical direction from a front end of the first region 121a. Accordingly, the first coupling piece 121 has an inversed 'L' shape. The first coupling piece 121 may be formed in pairs with the first support rod 120 interposed therebetween. The second support rod 140 has a second coupling piece 141 formed at a rear end spaced from the fixed magnet 130. The second coupling piece 141 may have the same structure as the first coupling piece 121.

Referring back to FIGS. 1 and 2, the fixed magnet 130 has a cylindrical shape and has a central axis disposed in parallel with the first direction X. The fixed magnet 130 has a structure in which the N pole and the S pole are bisected around the first direction X.

Spacers 135 and 136 are provided between the first support rod 120 and the fixed magnet 130 and between the fixed magnet 130 and the second support rod 140, respectively. The spacers 135 and 136 may have a predetermined thickness and have a radius corresponding to or greater than that of the fixed magnet 130. The spacers 135 and 136 may be formed of a nonmagnetic material. The spacers 135 and 136 block the fixed magnet 130 from being directly coupled to the first and second driving magnets 170 and 180 by a magnetic force. Accordingly, the first and second driving magnets 170 and 180 may be rotated by the control of an external magnetic field. In addition, the spacers 135 and 136 support ends of the first and second elastic bodies 190 and 210.

The first movable body 150 has a cylindrical shape with a predetermined length, and the first support rod 120 is inserted thereto. A first guide groove 151 and a first coupling groove 152 are formed in a side surface of the first movable body 150. Referring back to FIG. 4, the first guide groove 151 is formed along a longitudinal direction of the first movable body 150. The first coupling groove 152 is formed adjacent to the front end of the first movable body 150 and connected to the first guide groove 151. The first coupling groove 152 may extend perpendicular to the longitudinal direction of the first guide groove 151. The second region 121b of the first coupling piece 121 is positioned in the first coupling groove 152, so that the first coupling piece 121 may be coupled to the first coupling groove 152.

A first protrusion 154 is formed at the front end of the first movable body 150. The first protrusion 154 is formed in a radial direction along a circumference of an outer circumferential surface of the first movable body 150. The first protrusion 154 prevents the first elastic body 190 from being separated.

The second movable body 160 has a cylindrical shape with a predetermined length, and the second support rod 140 is inserted thereto. A second guide groove 161 and a second coupling groove 152 are formed in a side surface of the second movable body 160. the second guide groove 161 is formed along a longitudinal direction of the second movable body 160. The second coupling groove 162 is formed adjacent to a rear end of the second movable body 161 and connected to the second guide groove 161. The second coupling groove 162 may extend perpendicular to the longitudinal direction of the second guide groove 161. The second region 141b of the second coupling piece 141 is positioned in the second coupling groove 162, so that the second coupling piece 141 may be coupled to the second coupling groove 162.

A second protrusion 164 is formed at the rear end of the second movable body 160. The second protrusion 164 is formed in a radial direction along a circumference of an outer circumferential surface of the second movable body 160. The second protrusion 164 prevents the second elastic body 210 from being separated.

The first driving magnet 170 is fixedly coupled to a rear end of the first support rod 150 adjacent to the fixed magnet 130. The first driving magnet 170 has a cylindrical shape and has a central axis disposed in parallel with the first direction X. The first driving magnet 170 is inserted into the first support rod 120. The first driving magnet 170 has a structure in which the N pole and the S pole are bisected around the first direction X.

The second driving magnet 180 is fixedly coupled to a front end of the second support rod 160 adjacent to the fixed magnet 130. The second driving magnet 180 has a cylindrical shape and has a central axis disposed in parallel with the first direction X. The second driving magnet 180 is inserted into the second support rod 140. The first driving magnet 180 has a structure in which the N pole and the S pole are bisected around the first direction X.

According to the embodiment, the first driving magnet 170, the fixed magnet 130, and the second driving magnet 180 may have corresponding radii.

The first movable body 150 is inserted into the first elastic body 190, and one end of first elastic body 150 is supported by the first spacer 135 and the other end is supported by the first protrusion 154 of the first movable body 150. The first elastic body 190 is compressed when the first coupling piece 121 and the first coupling groove 152 are coupled to each other. When the coupling between the first coupling piece 121 and the first coupling groove 151 is released, the elastic force is delivered to the first protrusion 154, thereby providing a force for moving the first movable body 150.

The second movable body 150 is inserted into the second elastic body 210, and one end of second elastic body 120 is supported by the second spacer 136 and the other end is supported by the second protrusion 164 of the second movable body 160. The second elastic body 210 is compressed when the second coupling piece 141 and the second coupling groove 162 are coupled to each other. When the coupling between the second coupling piece 141 and the second coupling groove 162 is released, the elastic force is delivered to the second protrusion 164, thereby providing a force for moving the second movable body 160.

A first stent cover 220 has a cylindrical shape and is provided at a predetermined length in the first direction X. A length of the first stent cover 220 is provided to be shorter than a moving distance of the first movable body 150 when the first coupling piece 121 is released from the first coupling groove 152. A front end of the first stent cover 220 is coupled to the first protrusion 154 of the first movable body 150.

A second stent cover 230 has a cylindrical shape and is provided at a predetermined length in the first direction X. A length of the second stent cover 230 is provided to be shorter than a moving distance of the second movable body 160 when the second coupling piece 141 is released from the second coupling groove 162. A rear end of the second stent cover 230 is coupled to the second protrusion 164 of the second movable body 160.

The stent 20 is provided over the first elastic body 190, the fixed magnet 130, and the second elastic body 210, and surrounds the first elastic body 190, the fixed magnet 130, and the second elastic body 210. A front end of the stent 20 is accommodated in a space between the first stent cover 220 and the first elastic body 190, and a rear end thereof is accommodated in a space between the second stent cover 230 and the second elastic body 210.

Hereinafter, a method of expanding the stent using the above-described stent delivery device will be described.

Figure 5:
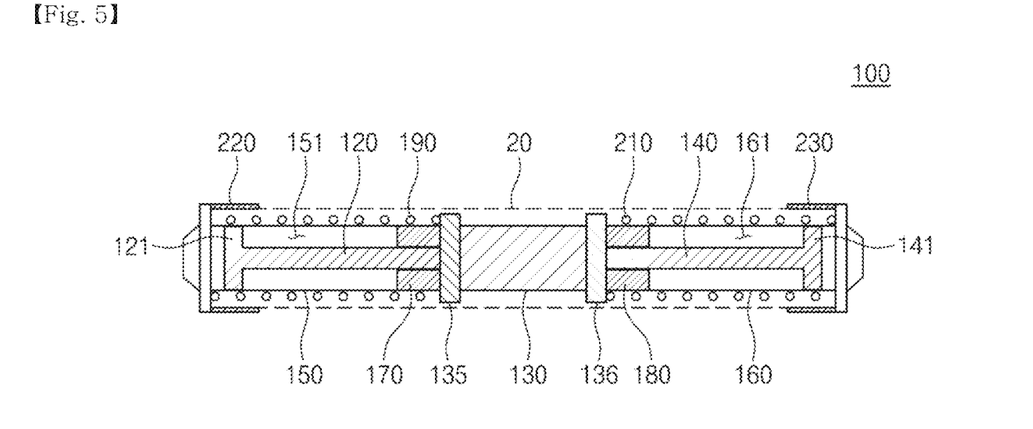
FIG. 5 is a view showing a process of transferring the stent by the stent delivery device.
Figure 6:
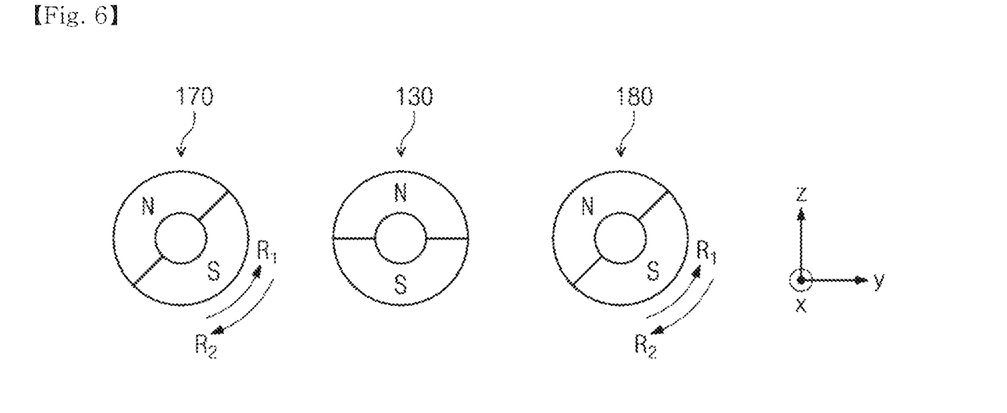
FIG. 6 is a view showing an arrangement of the first and second driving magnets and the fixed magnet.

FIG. 5 is a view showing a process of transferring the stent by the stent delivery device. FIG. 6 is a view showing an arrangement of the first and second driving magnets and the fixed magnet.

Referring to FIGS. 4 to 6, the stent delivery device 100 accommodates the stent 20 in a state in which the first coupling piece 121 is coupled to the first coupling groove 152, the second coupling piece 141 is coupled to the second coupling groove 162, and the first and second elastic bodies 190 and 210 are compressed. At this time as shown in FIG. 6, the polarities of the fixed magnet 130 and the polarities of the first and second driving magnets 170 and 180 are arranged in an unaligned state in the first direction X. Specifically, the polarities of the first and second driving magnets 170 and 180 may be arranged to be offset from the polarities of the fixed magnet 130 by a predetermined angle. The first and second driving magnets 170 and 180 generate magnetic torque in a first rotation direction R1 because the first and second driving magnets 170 and 180 try to maintain a magnetically stable state together with the fixed magnet 130. Even when the magnetic torque is applied, the rotations of the first and second movable bodies 150 and 160 are limited by the first and second coupling pieces 121 and 141. The magnetic torque R1 and the coupling pieces 121 and 141 are provided, so that the first and second movable bodies 150 and 160 may be stably restrained with the inner body 110. Meanwhile, when the external magnetic field is applied during moving the stent 20, a size of the external magnetic field is required to be controlled to prevent the magnetic torques acting on the first and second driving magnets 170 and 180 from being generated in a second rotation direction R2.

When the catheter 10 moves the stent delivery device 100 to a desired point, the expansion of the stent 20 proceeds.

Figure 7:
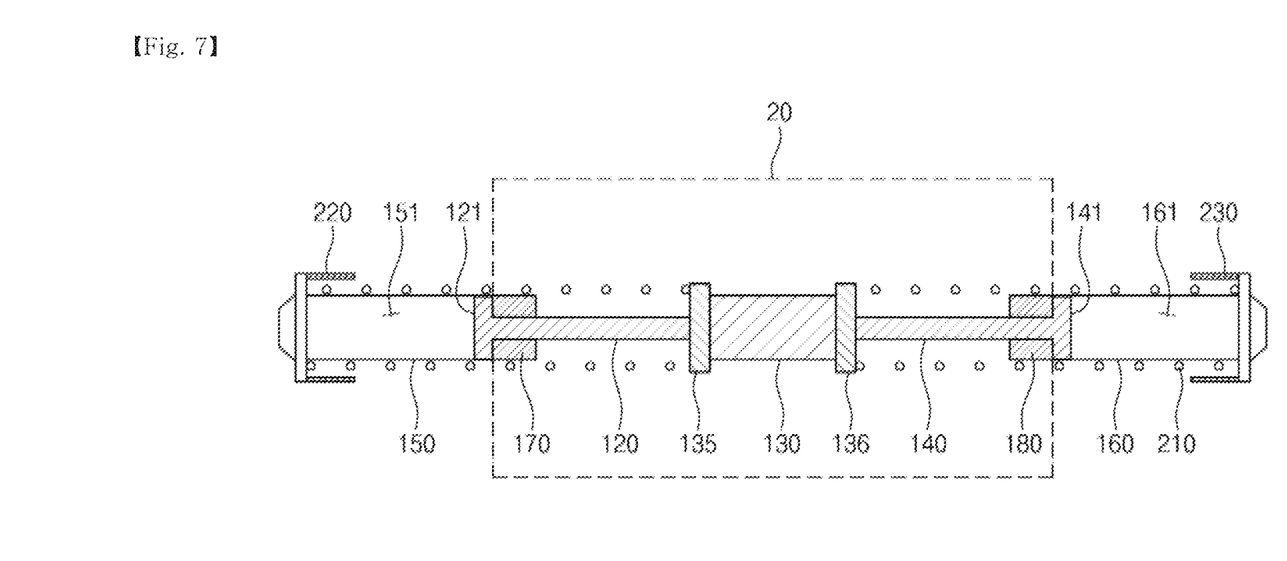
FIG. 7 is a view showing a state in which the stent delivery device expands the stent.
Figure 8:
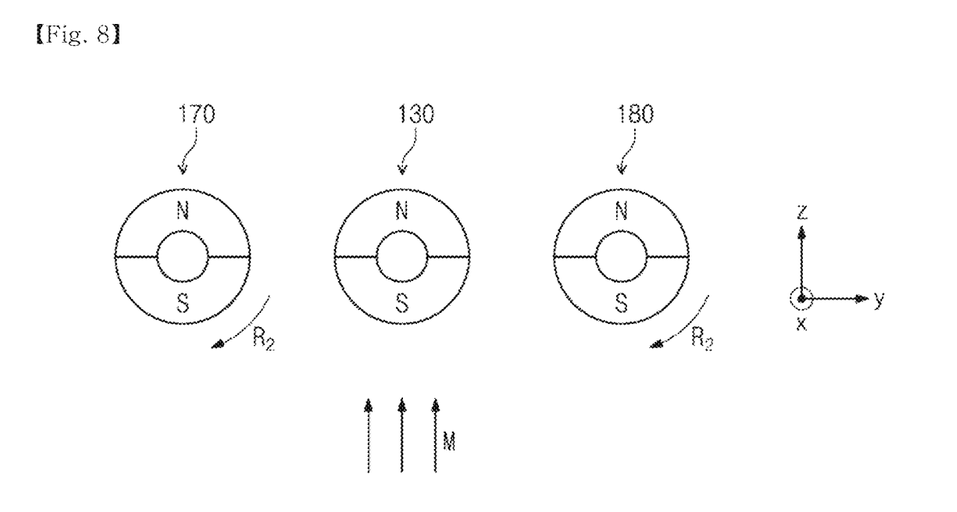
FIG. 8 is a view showing an arrangement of first and second driving magnets and the fixed magnet when the external magnetic field is applied.

FIG. 7 is a view showing a state in which the stent delivery device expands the stent. FIG. 8 is a view showing an arrangement of first and second driving magnets and the fixed magnet when the external magnetic field is applied.

Referring to FIGS. 7 and 8, the first and second driving magnets 170 and 180 are aligned in a direction of the external magnetic field when a strong external magnetic field M is applied. According to the embodiment, when the external magnetic field M is generated in the same direction as the polarity arrangement of the fixed magnet 130, the first and second driving magnets 170 and 180 are rotated in the second rotation direction R2 so as to be arranged in the same direction as the polarity of the fixed magnet 130. Accordingly, the first driving magnet 170, the fixed magnet 130, and the second driving magnet 180 are aligned with the same polarity along the first direction X.

The first and second movable bodies 150 and 160 are rotated in the second rotation direction R2 together with the first and second driving magnets 170 and 180. In the above process, the first and second coupling pieces 121 and 141 are released from the first and second coupling grooves 151 and 161.

The first and second movable bodies 150 and 160 move in a direction away from the fixed magnet 130 by the elastic force of the first and second elastic bodies 190 and 210. In the process of moving the first and second movable bodies 150 and 160, the first and second coupling pieces 121 and 141 are positioned in the first and second guide grooves 151 and 161, respectively, so that the first and second movable bodies 150 and 160 may linearly move.

The first and second stent covers 220 and 230 move together with the first and second movable bodies 150 and 160, in which the first and second stent covers 220 and 230 are separated from both ends of the stent 20, respectively, and the stent 20 having the released both ends is expanded.

Figure 9:
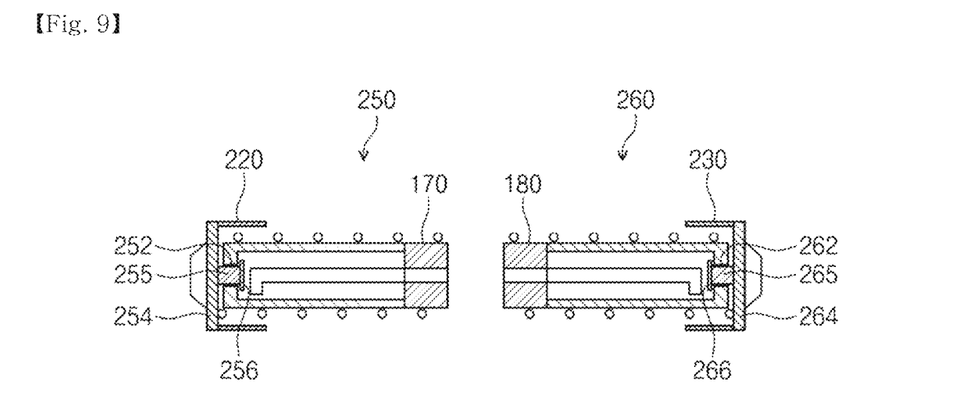
FIG. 9 is a sectional view showing the first and second movable body according to another embodiment of the present invention.

FIG. 9 is a sectional view showing the first and second movable body according to another embodiment of the present invention.

Referring to FIG. 9, the first movable body 250 is provided in a structure relatively rotatable with respect to the first protrusion 254 to which the first stent cover 220 is coupled. Specifically, an insertion hole 252 is formed at the front end of the first movable body 250, and a fitting portion 255 is formed in the first protrusion 254. The fitting portion 255 is inserted into the insertion hole 252, and has a diameter smaller than an inner diameter of the insertion hole 252. For this reason, the first protrusion 254 may be relatively rotated to the first movable body 250. In addition, the end 256 of the fitting portion 255 has a diameter greater than the inner diameter of the insertion hole 252. The end 256 of the fitting portion 255 prevents the fitting portion 255 from being separated.

The second movable body 260 is provided in a structure relatively rotatable with respect to the second protrusion 264 to which the second stent cover 230 is coupled. Specifically, an insertion hole 262 is formed at the rear end of the second movable body 260, and a fitting portion 265 is formed in the second protrusion 264. The fitting portion 265 is inserted into the insertion hole 262, and has a diameter smaller than an inner diameter of the insertion hole 262. For this reason, the second protrusion 264 may be relatively rotated to the second movable body 260. In addition, the end of the fitting portion 265 has a diameter greater than the inner diameter of the insertion hole 262. The end 266 of the fitting portion 265 prevents the fitting portion 265 from being separated.

When the first and second driving magnets 170 and 180 are rotated by the control of the external magnetic field so as to be arranged in the same direction as the polarities of the fixed magnet 130, the first and second protrusions 254 and 264 are not rotated, and only the first and second movable bodies 250 and 260 are relatively rotated.

As in the previous embodiment, when the first and second movable bodies 150 and 160 are integrally rotated with the first and second protrusions 154 and 164 upon the rotation of the first and second driving magnets 170 and 180, interference may occur between the first and second stent covers 220 and 230 and the stent 20 according to a gap between the first stent cover 220 and the first elastic body 190, and a gap between the second stent cover 230 and the second elastic body 210. A friction caused by the interference prevents the first and second driving magnets 170 and 180 from being smoothly rotated.

In order to solve the above problem, according to the present embodiment, the first movable body 250 and the second movable body 260 are separately from the first protrusion 254 and the second protrusion 264, respectively.

Accordingly, even when the interference with the stent 20 occurs, the first and second movable bodies 250 and 260 may be rotated relative to the first and second protrusions 254 and 264, so that the first and second driving magnets 170 and 180 may be smoothly rotated.

Although the present invention has been described in detail by using exemplary embodiments, the scope of the invention is not limited to the specific embodiments, and shall be interpreted by the appended claims. In addition, it will be apparent that a person having ordinary skill in the art may carry out various deformations and modifications for the embodiments described as above within the scope without departing from the present invention.

The stent delivery device according to the present invention may be used to improve stenosis or occlusion occurring in a body tubular cavity such as blood vessel, bile duct, bronchus, esophagus, and urethra.

What is claimed is:

1. A stent delivery apparatus comprising:
   an inner body in which a first support rod and a fixed magnet are coupled in a first direction; and
   a first movable body having inner space into which one end of the first support rod is inserted, and including a first driving magnet arranged at one end of the first movable body, which is adjacent to the fixed magnet;
   wherein a stent is coupled to surround the first movable body and the fixed magnet, and
   wherein by control of an external magnetic field, the first driving magnet rotate about the first direction with respect to the fixed magnet such that the same polarities thereof as the polarities of the fixed magnet are arranged in a row in a first direction.

2. The stent delivery apparatus of claim 1, wherein the inner body includes,
   a second support rod coupled to the fixed magnet in the first direction;
   wherein the stent delivery apparatus includes,
   a second movable body having inner space into which one end of the second support rod is inserted, and including a second driving magnet arranged at one end of the second movable body, which is adjacent to the fixed magnet;
   wherein the stent is coupled to surround the first movable body, the fixed magnet, and the second movable body,
   wherein by control of the external magnetic field, the second driving magnet rotates about the first direction with respect to the fixed magnet such that the same polarities thereof as the polarities of the fixed magnet are arranged in a row in the first direction.

3. The stent delivery device of claim 2, wherein the inner body further includes nonmagnetic spacers provided between the fixed magnet and the first driving magnet and between the fixed magnet and the second driving magnet, respectively.

4. The stent delivery device of claim 2, wherein a first coupling piece is formed in the first support rod, a first coupling groove is formed in the first movable body, a second coupling piece is formed in the second support rod, a second coupling groove is formed in the second movable body,
   wherein the stent delivery apparatus further comprises,
   a first elastic body having inner space into which the first movable body is inserted, compressed when the first coupling piece is coupled to the first coupling groove, and delivering an elastic force to the first movable body when the first coupling piece is released from the first coupling groove; and
   a second elastic body having inner space into which the second movable body is inserted, compressed when the second coupling piece is coupled to the second coupling groove, and delivering an elastic force to the second movable body when the second coupling piece is released from the second coupling groove.

5. The stent delivery device of claim 4, wherein a front end of the first movable body is formed with a first protrusion for supporting one end of the first elastic body, and a rear end of the second movable body is formed with a second protrusion for supporting one end of the second elastic body, in which the first movable body is relatively rotatable to the first protrusion, and the second movable body is relatively rotatable to the second protrusion.

6. The stent delivery device of claim 4, wherein polarity of the first driving magnet is arranged to be offset from polarity of the fixed magnet by a predetermined angle about the first direction when the first coupling piece is coupled to the first coupling groove; and
   polarity of the second driving magnet is arranged to be offset from the polarity of the fixed magnet by a predetermined angle about the first direction when the second coupling piece is coupled to the second coupling groove.

7. The stent delivery device of claim 4, wherein the first movable body is formed with a first guide groove provided in the first direction and connected to the first coupling groove, and the second movable body is formed with a second guide groove provided in the first direction and connected to the second coupling groove, in which the first coupling piece is positioned in the first guide groove when the first coupling piece is released from the first coupling groove, and the second coupling piece is positioned in the second guide groove when the second coupling piece is released from the second coupling groove.

8. The stent delivery device of claim 2, wherein each of the fixed magnet, the first driving magnet, and the second driving magnet is bisected into a North pole and a South pole about the first direction.

9. The stent delivery device of claim 2, further comprising:
   a first stent cover fixedly coupled to the opposite end of the first movable body to accommodate one end of the stent; and
   a second stent cover fixedly coupled to the opposite end of the second movable body to accommodate an opposite end of the stent.

* * * * *